United States Patent [19]

Gregory et al.

[11] Patent Number: 4,553,853

[45] Date of Patent: Nov. 19, 1985

[54] END POINT DETECTOR FOR A TIN LEAD EVAPORATOR

[75] Inventors: Joseph D. Gregory, Casanova, Va.; James M. Budnik, Essex Junction, Vt.

[73] Assignee: International Business Machines Corporation, Armonk, N.Y.

[21] Appl. No.: 584,072

[22] Filed: Feb. 27, 1984

[51] Int. Cl.[4] .......................................... G01N 25/10
[52] U.S. Cl. .................................... 374/25; 148/128; 373/136
[58] Field of Search ....................... 374/25, 16, 17, 26, 374/53; 356/43; 164/4.1; 373/117, 136; 148/128

[56] References Cited

U.S. PATENT DOCUMENTS

| | | | |
|---|---|---|---|
| 404,600 | 6/1889 | Caspersson | 374/53 |
| 2,127,889 | 8/1938 | Shenk et al. | 374/129 |
| 2,404,147 | 12/1941 | Strickland, Jr. | 219/50 |
| 2,535,855 | 12/1950 | Kurek | 374/25 X |
| 2,640,137 | 11/1950 | Ketchledge | 219/50 |
| 2,815,276 | 7/1955 | Michaux | 75/60 |
| 3,504,525 | 4/1970 | Ishii | 374/25 |
| 3,718,757 | 2/1973 | Gulitz et al. | 178/15 X |
| 3,745,834 | 7/1973 | Veltze et al. | 356/44 X |
| 3,891,834 | 6/1975 | Warsinksi | 374/26 X |
| 3,925,117 | 12/1975 | Stone et al. | 148/171 |
| 3,925,118 | 12/1975 | Hollan | 148/175 |
| 4,018,566 | 4/1977 | Zeuch et al. | 156/601 X |
| 4,020,695 | 5/1977 | Roney | 356/43 X |
| 4,046,509 | 9/1977 | Backerud | 374/25 X |
| 4,058,429 | 11/1977 | Duncan et al. | 356/72 |
| 4,166,378 | 9/1979 | Berger et al. | 374/10 |
| 4,229,412 | 10/1980 | Orths et al. | 422/80 |
| 4,258,003 | 3/1981 | Hurle et al. | 422/109 |
| 4,274,284 | 6/1981 | Hance | 374/139 |
| 4,355,907 | 10/1982 | Orths et al. | 374/139 |
| 4,443,118 | 4/1984 | Cure | 374/26 |
| 4,484,823 | 11/1984 | Peuker | 374/27 |

OTHER PUBLICATIONS

C. Carpenter, et al, "Two-Cycle Pb/Sn Solder Evaporation," IBM TDB, 12/81, p. 3393. IBM T.D. Bulletin, vol. 24, No. 7A.

J. Cosgrove, et al, "Single-Heater Multi-Material Evaporation Source," 5/82, pp. 6423-6425. IBM T.D. Bulletin, vol. 24, No. 12.

K. Beermunder, et al, "Thermocouple Heat Control Radiation Shield," 10/82, p. 2279. IBM T.D. Bulletin vol. 25, No. 5.

E. Brainard, et al, "Ramping Technique for Pb/Sn Evaporation," 2/83, pp. 4756-4757, IBM T.D. Bulletin, vol. 25, No. 9.

F. Hornbeck, et al, "Measurement of Temperature in Vacuum Deposition Apparatus," 2/83, p. 4512. IBM T.D. Bulletin, vol. 25, No. 9.

W. Brown, et al, "Lead/Copper/Tin Co-Evaporation Process System," 4/83, p. 6113. IBM T.D. Bulletin, vol. 25, No. 11B.

V. Marcotte, et al, "Enchanced E—Beam Evaporation of Tin," pp. 608-609. IBM Disclosure Bulletin, vol. 26, No. 2, Jul. 1983.

*Primary Examiner*—Daniel M. Yasich
*Attorney, Agent, or Firm*—Jesse L. Abzug; John E. Hoel

[57] ABSTRACT

A monitoring technique is disclosed for determining when the end point has been achieved in the evaporation of the constituents from an alloy such as a tin lead alloy. An optical pyrometer or other temperature sensing device, is focused on a crucible in which both tin and lead is being heated. Since, under vacuum conditions, lead evaporates at a lower boiling point than does tin, the temperature of the crucible will achieve a first temperature plateau while the lead is being evaporated. After the lead has been depleted in the crucible, the temperature of the crucible will rise to a higher temperature plateau at which the tin will evaporate. The output of the optical pyrometer is digitized and is applied to a microcomputer which periodically samples the temperature of the crucible. The microcomputer is programmed to identify the lower boiling plateau for the lead constituent, to detect the rise in temperature of the crucible after the lead has been depleted, and to recognize the higher boiling point plateau for the tin constituent. The microcomputer will then output a signal to turn off the heating source to the crucible when the temperature of the crucible is detected to rise after the second, higher boiling point plateau for the tin.

5 Claims, 3 Drawing Figures

1

END POINT DETECTOR FOR A TIN LEAD EVAPORATOR

FIELD OF THE INVENTION

The invention disclosed broadly relates to measurement techniques, and more particularly relates to an improved technique for detecting when a constituent of an alloy has evaporated during a heating process.

BACKGROUND OF THE INVENTION

Metal structures are typically deposited on integrated circuits during their manufacture, by exposing the integrated circuit in a vacuum chamber to a source of the metal vapor. Vacuum evaporation of metals is achieved by placing the metal in a crucible within the vacuum chamber and heating the crucible until the metal reaches its boiling point. The liquid metal changes phase by absorbing the heat of vaporization from the heating source, and evaporates producing a cloud of the metal atoms in a vapor form which deposits on all exposed surfaces. Generally, refractory metal crucibles are employed for this purpose, which are composed of tantalum, platinum, or other suitable material. Crucibles made from such materials are relatively expensive and therefore it is important not to allow the crucible to be overheated after the contents of the crucible has evaporated. Not only does the excessive heating of the crucible produce a high temperature which physically destroys the crucible, but such inadvertently high temperatures will also cause the material of the crucible to itself evaporate, thereby contaminating the integrated circuit structures exposed.

One technique in the prior art to prevent the overheating of crucibles in a vacuum evaporation chamber, is to detect the end point of the evaporation of the contents of the crucible by visual inspection. Typically, a transparent celluloid film will be exposed to the evaporative metal cloud from the crucible on the inside of the vacuum chamber over a viewing window through the sidewall of the chamber. The operator of the chamber will observe the amount of deposition of metal vapor on the celluloid film at various times and when the operator judges that no more metal is being deposited onto the transparent film, the operator will turn off the heating source to the crucible. Not only is this form of inspection by the operator labor intensive, but it also produces an inaccurate and nonreproducible determination of the end point for the evaporation of the contents of the crucible. Since the quantity of material which is to be evaporated from the crucible is carefully calculated to enable the deposition of a desired thickness of resultant metal film on the integrated circuit, it is important to completely evaporate the contents of the crucible, and yet as was described above, it is also important not to extend the application of heat to the crucible, thereby destroying the crucible and possibly contaminating the resultant integrated circuit metal structures.

OBJECTS OF THE INVENTION

It is therefore an object of the invention to provide an improved technique for determining the end point for a vacuum evaporation process.

It is another object of the invention to provide an improved technique for increasing the precision with which the end point of an evaporation process is detected.

It is still a further object of the invention to provide an improved technique for detecting the end point in an evaporation process, which is less labor intensive than was required in the prior art.

It is still a further object of the invention to provide an improved end point detection technique for a vacuum evaporation process, which prolongs the useful life of crucibles used therein.

SUMMARY OF THE INVENTION

These and other objects, features and advantages of the invention are accomplished as disclosed herein. A monitoring technique is disclosed for determining when the end point has been achieved in the evaporation of the constituents from an alloy such as a tin lead alloy. An optical pyrometer or other temperature sensing device, is focused on a crucible in which both tin and lead is being heated. Since, under vacuum conditions, lead evaporates at a lower boiling point than does tin, the temperature of the crucible will achieve a first temperature plateau while the lead is being evaporated. After the lead has been depleted in the crucible, the temperature of the crucible will rise to a higher temperature plateau at which the tin will evaporate. The output of the optical pyrometer is digitized and is applied to a microcomputer which periodically samples the temperature of the crucible. The microcomputer is programmed to identify the lower boiling plateau for the lead constituent, to detect the rise in temperature of the crucible after the lead has been depleted, and to recognize the higher boiling point plateau for the tin constituent. The microcomputer will then output a signal to turn off the heating source to the crucible when the temperature of the crucible is detected to rise after the second, higher boiling point plateau for the tin.

DESCRIPTION OF THE FIGURES

These and other objects, features and advantages of the invention will be more fully appreciated with reference to the accompanying figures.

DISCUSSION OF THE PREFERRED EMBODIMENT

Figure 1:
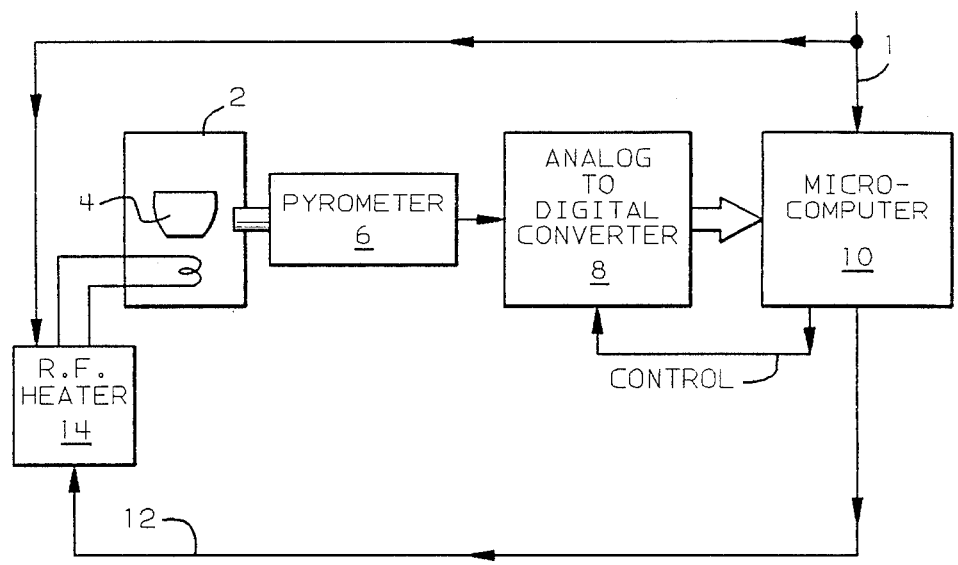
FIG. 1 is a functional block diagram of the end point detector invention.
Figure 2:
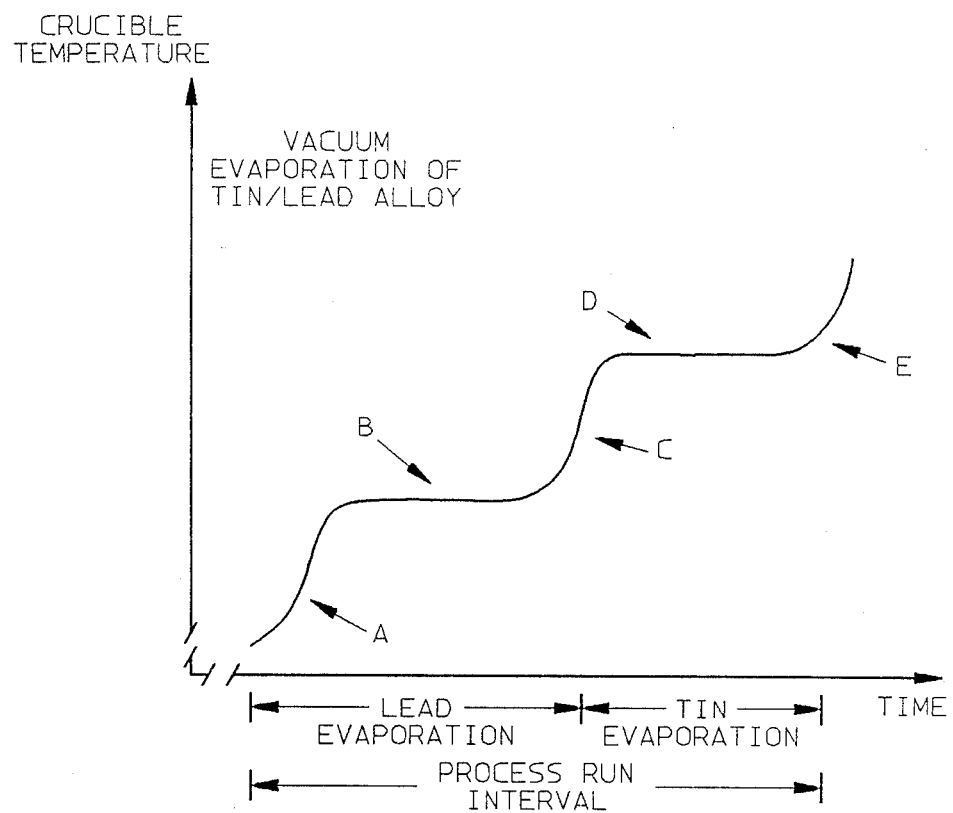
FIG. 2 is a graph of the relative temperature measured by the end point detector invention, as a function of time during the heating cycle for a two component alloy.

FIG. 1 is an overall functional block diagram of the invention. In a metal evaporating chamber, such as the vacuum chamber 2 shown in FIG. 1, a crucible 4 is heated by a radio frequency heater 14 so as to raise the temperature of the metal or metal mixture therein to the evaporation point for evaporative deposition of the metal onto a target. In the particular application here, a combination of tin and lead is melted in the crucible 4. Since, under vacuum conditions, lead has a lower boiling temperature, the lead will evaporate before the tin evaporates from the crucible. Reference to FIG. 2 will illustrate the variation of temperature with respect to time of the crucible 4 as the lead evaporates from the crucible followed by the tin evaporating from the crucible. A problem arises in determining when all of the lead and all of the tin has evaporated from the crucible, because after that time, the temperature of the crucible rises rapidly which can cause catastrophic destruction of the crucible structure. The approach for solving this problem is shown in FIG. 1, wherein an optical pyrometer 6 is positioned proximate to the bottom of the crucible 4. The pyrometer 6 monitors the absolute temperature of the crucible 4 and applies an analog voltage signal to the analog-to-digital converter 8 which periodically samples the analog signal and converts it to a sequence of digital values whose numerical magnitude is proportional to the temperature sensed by the pyrometer 6. This sequence of numerical values are input as sampled data to the microcomputer 10.

In operation, at the beginning of the process run interval, a start signal is input at 1 to the microcomputer 10 at the time that the RF heater 14 is turned on in the chamber 2. The temperature of the bottom of crucible 4 is monitored by the optical pyrometer 6 and the respective portions of the curve shown in FIG. 2 are identified. In particular, a first portion of the curve at A is the initial rise in temperature of the crucible in order to raise its temperature to the evaporation point for lead. The evaporation temperature for lead is shown at the plateau portion B of the curve in FIG. 2, which remains in effect until nearly all of the lead in the crucible has been evaporated. Then, the temperature of the crucible rises as is shown at C in FIG. 2, to the next plateau D which is the temperature of evaporation for the tin constituent in the crucible 4. After approximately 15 minutes, the tin has completely evaporated and it is at this critical time that the monitoring of the crucible 4 becomes critical. This is because the temperature of the crucible rapidly rises at E, as is shown in FIG. 2, and if the RF heater 14 in the chamber 2 has not turned off at this time, damage can result to the crucible 4.

Figure 3:
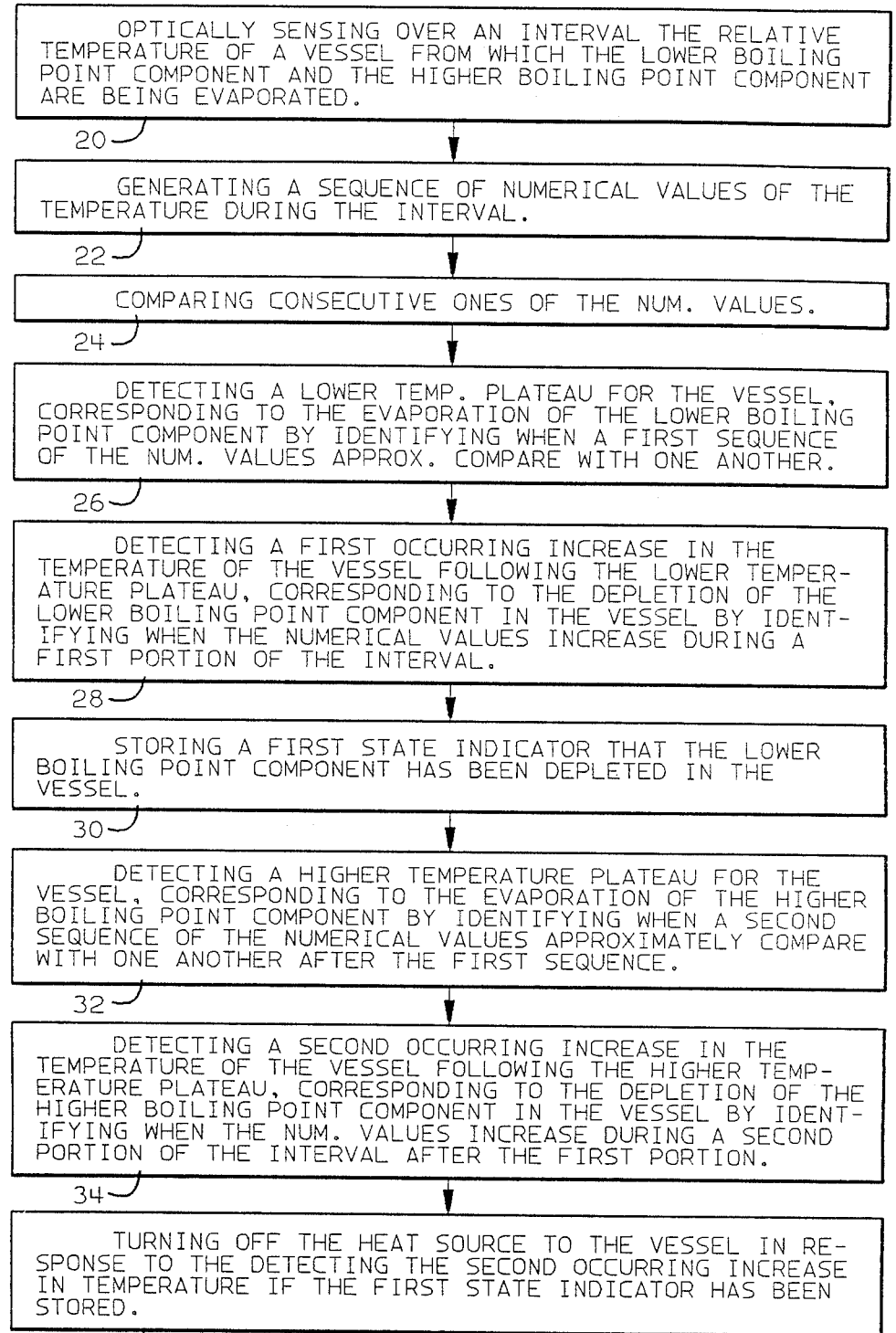
FIG. 3 is a flow diagram of the method which is performed by the apparatus shown in FIG. 1, in order to carry out the end point detection technique in accordance with the invention.

The monitoring operation for determining the portions A through E of the curve of FIG. 2 is achieved by means of the method outlined in the flow diagram of FIG. 3. At the beginning, the microcomputer 10 passes through some initialization stages and then is in a halt state until the RF heater 14 is turned on. Thereafter, the clock for the microcomputer 10 is initialized and started and the values for the temperature of the crucible output by the optical pyrometer 6 are repeatedly sampled by the analog-to-digital converter and monitored by the microcomputer. At each sampling interval, the current temperature is compared in the microcomputer with the prior temperature to determine if the first plateau has been reached at B in FIG. 2. After the first plateau has been reached, the algorithm in the microcomputer 10 continues to monitor the temperature until the second plateau at D has been reached. After the second plateau has been reached at D, the microcomputer 10 monitors the temperature values output by the pyrometer 6, looking for a rapid rate of change of the temperature with respect to time. When that rapid rate of change of temperature is determined, that indicates that the end point has been reached for the evaporation cycle, and the crucible is now empty and is rapidly rising in temperature. When this is determined by the microcomputer 10, a stop signal is output at 12 from the microcomputer 10 to the RF heater 14 in the chamber 2, turning it off.

In this manner, the power input to the crucible is turned off before damage can occur.

More specifically, FIG. 3 is a flow diagram of the method for detecting the end point in the evaporation of a two component alloy, each component having a different boiling point.

In step 20, the optical pyrometer 6 is optically sensing over a process run interval the relative temperature of the crucible vessel 4 from which the lower boiling point component and the higher boiling point component are being evaporated.

In step 22, the analog-to-digital converter 8 is generating a sequence of numerical values of the temperature during the interval.

In step 24, the microcomputer 10 is comparing consecutive pairs of the numerical values.

In step 26, the microcomputer 10 is detecting the lower temperature plateau B for the crucible 4, corresponding to the evaporation of the lower boiling point component by identifying when a first sequence of the numerical or indicator values output from the converter 8 are approximately equal to one another.

In step 28, the microcomputer 10 is detecting the first occurring increase C in the temperature of the crucible following the lower temperature plateau B, corresponding to the depletion of the lower boiling point component in the crucible, by identifying when the numerical values output from the converter 8 increase during a first portion of the process run interval.

In step 30, the microcomputer 10 is storing a first state indicator that the lower boiling point component has been depleted in the crucible 4.

In step 32, the microcomputer 10 is detecting the higher temperature plateau D for the crucible, corresponding to the evaporation of the higher boiling point component by identifying when a second sequence of the numerical values output from the converter 8 are approximately equal to one another after the first sequence.

In step 34, the microcomputer 10 is detecting the second occurring increase E in the temperature of the crucible following the higher temperature plateau D, corresponding to the depletion of the higher boiling point component in the crucible, by identifying when the numerical values output from converter 8 increase during a second portion of the process run interval after the first portion of the interval has occurred.

In step 36, the microcomputer 10 sends a signal 12 turning off the heat source 14 to the crucible in response to detecting the second occurring increase E in temperature, if the first state indicator was stored by the microcomputer 10 in step 30.

By virtue of monitoring the rate of change of temperature as opposed to the absolute value of the temperature output by the optical pyrometer 6, the system can be applied to measuring the temperature of crucibles in a variety of evaporation chambers, having different thermal conduction properties. Thus, even though the absolute temperature of a crucible at the end point may be different depending upon the particular evaporation chamber in which the measurements are being made, an accurate determination of the end point can still be obtained.

Still further, since the rate of evaporation can differ depending upon the rate of power input to the crucible and other thermal and power input variables, the duration of the evaporation cycle can be different. This does not influence the character of the monitoring of the end point, since it is once again, the rate of change of the temperature during the transition from the various plateaus in FIG. 2, which is established as the marking point for the various stages of the evaporation cycle.

Alternate heating techniques for the crucible can be employed in addition to the preferred embodiment which is radio frequency induction heating. For example, radiation heating by laser or solar sources or by gas discharge lighting can be employed. In addition, electron beam, plasma, or resistive heating can be used to raise the temperature of the crucible. In all cases, when the end point detector invention detects portion E of FIG. 2, a disabling signal will be sent to the heating source to turn it off so that the crucible will not be overheated.

The applications for the end point detector invention can be expanded beyond the detection of the end point in the evaporation of a two component alloy, as described above. For example, a single element constituent can be heated in the crucible and the end point of its transition from the solid state phase to the liquid phase or alternately from the liquid phase to the vapor phase can be detected by programming the microcomputer 10 in the end point detector invention to detect the portion C of the curve shown in FIG. 2. Still further, other alloy compositions can have their end point detected for vacuum evaporation purposes, for example alloys of lead and indium would also be amenable to end point detection by the invention disclosed herein. Alternately, an alloy or mixture of N constituents (where N is greater than 1) can have its end point detected, where each constituent has a different boiling point. Still further, techniques for the fractional distillation in the purification of metals can profit by applying the end point detector invention disclosed herein. The point at which a particular elemental constituent has been evaporated from a given alloy or mixture composition, can be determined by identifying the portion of the curve C in FIG. 2 beyond the plateau B in FIG. 2 corresponding to the evaporation of that fractionally separated constituent. If the percentage of the fractionally distilled constituent is relatively small in the composition, the sampling rate of the analog-to-digital converter 8 for the end point detector invention can be made faster so that the beginning of the portion C of the curve in FIG. 2 beyond the portion B corresponding to the element to be detected, can be rapidly identified. This is necessary since the duration for the plateau portion B in FIG. 2 for a particular constituent in a composition is approximately proportional to the relative proportion of that constituent in the composition. Thus, if a relatively small percentage of the composition is represented by the constituent, the duration of the plateau portion B of FIG. 2 is relatively short and thus a higher frequency is necessary in the sampling rate in order to accurately identify the inflection point where the portion C of FIG. 2 begins.

Although a specific embodiment of the invention has been disclosed, it will be understood by those of skill in the art that various changes can be made in the form and details of the invention so disclosed, without departing from the spirit and the scope of the invention.

We claim:

1. A method for detecting the end point in the evaporation of a two component alloy in a chamber, each component having a different boiling point, comprising the steps of:

optical sensing the relative temperature of a heated vessel from which the lower boiling point component and the higher boiling point component are being evaporated;

detecting a lower temperature plateau for said vessel, corresponding to the evaporation of said lower boiling point component;

detecting a first occurring increase in the temperature of said vessel following said lower temperature plateau, corresponding to the depletion of said lower boiling point component in said vessel;

detecting a higher temperature plateau for said vessel, corresponding to the evaporation of said higher boiling point component;

detecting a second occurring increase in the temperature of said vessel following said higher temperature plateau, corresponding to the depletion of said higher boiling point component in said vessel;

turning off a heat source to said vessel in response to said detecting said second occurring increase in temperature.

2. A method for detecting the end point in the evaporation of a two component alloy in an evaporating chamber, each component having a different boiling point, comprising the steps of:

sensing the relative temperature of a heated vessel in the chamber, from which the lower boiling point component and the higher boiling point component are being evaporated, with a pyrometer;

detecting a lower temperature plateau for said vessel, corresponding to the evaporation of said lower boiling point component;

detecting a first occurring increase in the temperature of said vessel following said lower temperature plateau, corresponding to the depletion of said lower boiling point component in said vessel;

storing a first state temperature indicator value that said lower boiling point component has been depleted in said vessel;

detecting a higher temperature plateau for said vessel, corresponding to the evaporation of said higher boiling point component;

detecting a second occurring increase in the temperature of said vessel following said higher temperature plateau, corresponding to the depletion of said higher boiling point component in said vessel; and turning off a heat source to said vessel in response to said detecting said second occurring increase in temperature.

3. A method for detecting the end point in the evaporation of an N component alloy in a chamber, each component having a different boiling point, N being greater than 1, comprising the steps of:

sensing the relative temperature of a heated vessel from which N different boiling point components are being evaporated;

detecting a lower temperature plateau for said vessel, corresponding to the evaporation of said first boiling point component;

detecting a first occurring increase in the temperature of said vessel following said lower temperature plateau, corresponding to the depletion of said first boiling point component in said vessel;

repeating said detecting steps for a next higher boiling point component of said vessel;

detecting an $N^{th}$ highest temperature plateau for said vessel, corresponding to the evaporation of said $N^{th}$ highest boiling point component;

detecting an $N^{th}$ occurring increase in the temperature of said vessel following said $N^{th}$ highest temperature plateau, corresponding to the depletion of said $N^{th}$ boiling point component in said vessel;

turning off a heat source to said vessel in response to said detecting said N$^{th}$ occurring increase in temperature.

4. A method for detecting the end point in the evaporation of a two component alloy in a chamber, each component having a different boiling point, comprising the steps of:

optically sensing the relative temperature of a heated vessel from which the lower boiling point component and the higher boiling point component are being evaporated;

detecting a lower temperature plateau for said vessel, corresponding to the evaporation of said lower boiling point component;

detecting a first occurring increase in the temperature of said vessel following said lower temperature plateau, corresponding to the depletion of said lower boiling point component in said vessel;

detecting a higher temperature plateau for said vessel, corresponding to the evaporation of said higher boiling point component;

detecting a second occurring increase in the temperature of said vessel following said higher temperature plateau, corresponding to the depletion of said higher boiling point component in said vessel;

turning off a heat source to said vessel in response to said detecting said second occurring increase in temperature.

5. A computer method for detecting the end point in the evaporation of a two component alloy in a chamber, each component having a different boiling point, comprising the steps of:

optically sensing over an interval the relative temperature of a vessel from which the lower boiling point component and the higher boiling point component are being evaporated;

providing a sequence of numerical values of said temperature during said interval;

comparing consecutive ones of said numerical values with each other by a computer;

detecting a lower temperature plateau for said vessel, corresponding to the evaporation of said lower boiling point component by identifying when a first sequence of said numerical values approximately compare with one another;

detecting a first occurring increase in the temperature of said vessel following said lower temperature plateau, corresponding to the depletion of said lower boiling point component in said vessel by identifying when said numerical values increase during a first portion of said interval;

storing a first state indicator value that said lower boiling point component has been depleted in said vessel;

detecting a higher temperature plateau for said vessel, corresponding to the evaporation of said higher boiling point component by identifying when a second sequence of said numerical values approximately compare with one another after said first sequence;

detecting a second occurring increase in the temperature of said vessel following said higher temperature plateau, corresponding to the depletion of said higher boiling point component in said vessel by identifying when said numerical values increase during a second portion of said interval after said first portion; and turning off a heat source to said vessel in response to said detecting said second occurring increase in temperature.

* * * * *